(12) United States Patent
Rhoads et al.

(10) Patent No.: US 9,621,760 B2
(45) Date of Patent: Apr. 11, 2017

(54) INFORMATION CODING AND DECODING IN SPECTRAL DIFFERENCES

(71) Applicant: Digimarc Corporation, Beaverton, OR (US)

(72) Inventors: Geoffrey B. Rhoads, West Linn, OR (US); Alastair M. Reed, Lake Oswego, OR (US)

(73) Assignee: Digimarc Corporation, Beaverton, OR (US)

( * ) Notice: Subject to any disclaimer, the term of this patent is extended or adjusted under 35 U.S.C. 154(b) by 356 days.

(21) Appl. No.: 14/298,747

(22) Filed: Jun. 6, 2014

(65) Prior Publication Data

US 2015/0071485 A1    Mar. 12, 2015

Related U.S. Application Data

(63) Continuation-in-part of application No. 14/201,852, filed on Mar. 8, 2014.
(Continued)

(51) Int. Cl.
*G06K 9/00* (2006.01)
*H04N 1/32* (2006.01)
(Continued)

(52) U.S. Cl.
CPC ........ *H04N 1/32309* (2013.01); *G01J 3/0272* (2013.01); *G01J 3/2823* (2013.01); *G01J 3/36* (2013.01); *G01J 3/447* (2013.01); *G01J 3/51* (2013.01); *G01J 3/513* (2013.01); *G06T 1/0028* (2013.01); *H04N 1/32144* (2013.01); *H04N 5/2254* (2013.01); *H04N 5/2256* (2013.01); *H04N 5/2354* (2013.01); *H04N 9/045* (2013.01); *H04N 21/8358* (2013.01); (Continued)

(58) Field of Classification Search
None
See application file for complete search history.

(56) References Cited

U.S. PATENT DOCUMENTS 7,922,209 B1 *  4/2011  Beretta ................. B42D 25/29
                                                    283/107
7,938,331 B2    5/2011  Brock et al.
(Continued)

FOREIGN PATENT DOCUMENTS

WO    WO2012047340    4/2012
WO    WO2013/109934   7/2013

OTHER PUBLICATIONS

International Search Report and Written Opinion dated Oct. 24, 2014 from PCT/US2014/041417.
(Continued)

*Primary Examiner* — Weiwen Yang
(74) *Attorney, Agent, or Firm* — Digimarc Corporation (57) ABSTRACT

Information is encoded in an image signal by exploiting spectral differences between colors that appear the same when rendered. These spectral differences are detected using image sensing that discerns the spectral differences. Spectral difference detection methods include using sensor-synchronized spectrally-structured-light imaging, 3D sensors, imaging spectrophotometers, and higher resolution Bayer pattern capture relative to resolution of patches used to convey a spectral difference signal.

22 Claims, 2 Drawing Sheets

Related U.S. Application Data (60) Provisional application No. 61/832,752, filed on Jun. 7, 2013, provisional application No. 61/907,362, filed on Nov. 21, 2013.

(51) Int. Cl.

| | | |
|---|---|---|
| *G01J 3/51* | (2006.01) | |
| *G01J 3/28* | (2006.01) | |
| *G01J 3/36* | (2006.01) | |
| *G01J 3/447* | (2006.01) | |
| *H04N 5/225* | (2006.01) | |
| *H04N 5/235* | (2006.01) | |
| *H04N 9/04* | (2006.01) | |
| *G01J 3/02* | (2006.01) | |
| *H05B 33/08* | (2006.01) | |
| *H05B 37/02* | (2006.01) | |
| *G06T 1/00* | (2006.01) | |
| *H04N 21/8358* | (2011.01) | |
| *A61B 5/00* | (2006.01) | |

(52) U.S. Cl.
CPC ..... *H05B 33/0869* (2013.01); *H05B 37/0272* (2013.01); *A61B 5/0075* (2013.01); *G06T 2201/0051* (2013.01); *H04N 2201/3233* (2013.01)

(56) References Cited

U.S. PATENT DOCUMENTS

| | | |
|---|---|---|
| 8,224,018 B2 | 7/2012 | Rhoads et al. |
| 8,888,207 B2 | 11/2014 | Furness, III et al. |
| 2004/0263911 A1 | 12/2004 | Rodriguez et al. |
| 2006/0115110 A1* | 6/2006 | Rodriguez ............... B41M 3/10 382/100 |
| 2007/0143232 A1 | 6/2007 | Auslander et al. |
| 2008/0112596 A1 | 5/2008 | Rhoads et al. |
| 2010/0142003 A1 | 6/2010 | Braun et al. |
| 2010/0150396 A1 | 6/2010 | Reed |
| 2010/0150434 A1 | 6/2010 | Reed |
| 2011/0007935 A1 | 1/2011 | Reed et al. |
| 2011/0098029 A1 | 4/2011 | Rhoads et al. |
| 2011/0212717 A1 | 9/2011 | Rhoads et al. |
| 2012/0243009 A1 | 9/2012 | Chapman et al. |
| 2013/0329006 A1 | 12/2013 | Boles et al. |

OTHER PUBLICATIONS

International Search Report and Written Opinion dated Nov. 4, 2014 from PCT/US2014/050573.

Willis et al., "InfraStructures", ACM Transactions on Graphics, vol. 32, No. 4, Jul. 1, 2013.

Silverbrook Research U.S. Appl. No. 61/350,013, filed May 31, 2010.

Office Action dated Jul. 17, 2013, in U.S. Appl. No. 13/444,521.

U.S. Appl. No. 13/888,939, filed May 7, 2013.

\* cited by examiner

INFORMATION CODING AND DECODING IN SPECTRAL DIFFERENCES

RELATED APPLICATION DATA

This application claims the benefit of U.S. Provisional Application No. 61/832,752, filed Jun. 7, 2013, which is hereby incorporated by reference. This application also claims the benefit of U.S. Provisional Application No. 61/907,362, filed Nov. 21, 2013.

This application is also a continuation in part of U.S. application Ser. No. 14/201,852, filed Mar. 8, 2014 (US Application Publication 2014-0293091). All of the above applications are incorporated by reference herein.

TECHNICAL FIELD

The invention relates to image signal processing, and relates to information encoding and decoding within image signals. The invention also relates to light sources and image sensing, and signal detection using combinations of light sources and image sensing to discern spectral properties.

BACKGROUND AND SUMMARY

Information coding in image signals has a broad array of applications, and there many techniques for accomplishing it. The information coding may be visible or hidden from human perception when the imagery conveying the data is rendered. It may be incorporated in various forms of electromagnetic-signals that convey visual content, such as digital images or video. It may also be transferred to a physical object through image projection, printed inks or other data writing techniques, such as engraving, etching, molds, etc.

Images with coded information are captured from objects or signals and processed to extract the coded information. The capture process may use special purpose devices, such as bar coding reading equipment, or general purpose image capture devices, such as cameras and scanners. The captured image signal is then processed to recover the coded information. The coded information, itself may encompass various forms of information, including other images (e.g., images of text or graphics encoded within a host image), audio, or machine readable data streams.

Digital watermarking is an information coding field that applies to many forms of signals, with one significant subset being images. In this field, sometimes more generally referred to as steganography, researchers have long sought to increase the capacity and robustness of information capacity of the channel within an image signal, while making the presence of information imperceptible to humans, and the signal processing to encode and decode this information computationally efficient. While the field is well-developed, and various implementations have been widely deployed, these fundamental challenges remain.

The desire to achieve imperceptibility has led researchers to study the human visual system to determine ways in which information may be encoded efficiently, reliably, yet imperceptibly. Practical applications dictate constraints that make this task difficult. One can achieve imperceptibility, even with well-known message coding symbologies like bar codes, by printing or projecting signals in a physical media that are outside human perception, yet can be detected by special purpose illumination and image capture, e.g., using Ultraviolet or Infrared related techniques. These techniques, of course, tend to preclude broad application to devices that operate in the visible spectrum. Preferably, to have broader application, the information coding technique should not require special materials or illumination-capture techniques.

The study of the human visual system, particularly in field of digital watermarking, has led to the development of various masking models. These models are used to determine the ability of image signals to mask other image signals. They are adapted for various types of applications, such as electronic displays, print quality, and are also adapted for static and time varying images (video). Various attributes of image content are evaluated to assess masking capability of an image for certain other image signal types. Some attributes include signal activity or noisiness, color, resolution, contrast, and motion. These attributes, have various masking capability on image content with like or different quantities of these attributes. Various signal transforms are used to convert an image into transform domain coefficients, such as various forms of decomposition into coefficients or sub-bands, to examine various image attributes at spatial frequencies.

One goal of this particular research, particularly as it relates to encoding auxiliary information, is to determine an information channel within an image in which changes to the image may be made with little or no impact on the visual appearance of the image to a human. Preferably, this channel should remain within the space of image variables that are typically available and controllable to enable auxiliary information encoding using digital signal processing on standard image formats. For example, color image signals are typically represented as arrays of pixels, with each pixel represented using three or more image variables, such as Red, Green, Blue values (RGB), or Cyan, Magenta, Yellow, and black (CMYK). Some formats define pixels in terms of luminance, chrominance, hue, intensity and/or saturation. There are a variety of formats for digital representation of image signals based on these or other variables. Information coding that operates on images of these formats derives masking models and adjusts values of these variables or parameters derived from them, to encode auxiliary information.

For certain application domains, such as information channels in printed images, additional degrees of freedom may be obtained by controlling the selection and application of inks. Printer manufacturers can, for example, build the capability to control the depth, shape, spatial arrangement of ink over a unit of area corresponding to a digital pixel or groups of pixels. The degrees of freedom expand across the colors, and combination of inks that represent each of them. Various half-toning techniques are used to convert digital pixel values into a format for controlling application of ink to various types of paper. See, for example, our pending application, 61/719,920, AUXILIARY DATA EMBEDDING IN RASTER IMAGE PROCESSOR AND IMAGE RECOGNITION, filed Oct. 29, 2012, and its counterpart, Ser. No. 13/789,126, published as US Patent Application Publication No. 2014-0119593, which are hereby incorporated by reference.

Likewise, greater control may also be provided over conversion of image signals into analog form via display or projection. As in the case of printing, this affords greater flexibility in the encoding technology. However, access to this control is not always available. Information coding that does not rely on this additional control over how images are represented and rendered have the advantage of broader applicability across a range of devices and systems.

Another constraint for many applications, as noted above, is that the information coding technique must produce an information signal in the image that can be "seen" by the capture device. Use of special inks have value for some applications, like counterfeit deterrence, yet do not allow the signal to be communicated through typical cameras that operate in the visible light range (e.g., those now ubiquitous on mobile phones, tablets and PCs).

The application of color science has offered promising advances in information coding in images. Changes in some colors are more noticeable than others to the typical human. By combining these phenomena with other masking techniques, additional information signals may be encoded within a desired perceptibility threshold. This observation has led to the development of image coding techniques that exploit it. See, for example, our US Patent Publication 20110216936.

Within the field of color science, metamerism refers to the matching of colors that appear similar to humans, yet have different spectral power distributions. This property may have promise in information coding within images, as it offers the potential of using colors with different spectral distributions as means to encode information within an image. These colors appear the same to humans, yet have differences that are detectable given the appropriate capture and signal processing that can discern the signal in the differences between spectral distributions of colors sensed from an object or image. In order to make this available using a wide array of image types, there is need for techniques to encode auxiliary information in spectral differences that can apply to standard image formats and commonly used image rendering technology (e.g., image printers, displays, projection systems, etc.). Further, there is a need for sensors and/or signal processing techniques that can discern spectral differences sufficiently to recover the information encoded in these differences.

In this document, we describe a variety of inventive methods and related hardware components for information coding in spectral differences in images. Some of these methods are implemented using digital image processing to alter pixel values within digital images in standard color formats. Of course, with greater control over the variables and materials used to render images, a much broader range of techniques may be implemented using spectral difference principles, yet extending them in rendering systems that offer access to more colors, and more control over rendering them into image output.

We also describe a variety of inventive methods and related hardware components for the complementary technology of determining spectral distributions, discerning spectral differences, and decoding information encoded in those spectral differences.

Our prior application Ser. Nos. 13/840,451 and 14/201, 852, entitled Sensor-Synchronized Spectrally-Structured-Light Imaging, describe a variety of image capture technology and methods that can be used to determine a spectral distribution of colors at areas within an image. These application Ser. No. 13/840,451 (now published as US Patent Application Publication No. 2013-0308045) and Ser. No. 14/201,852, are incorporated by reference in their entirety. The spectral distribution corresponds to measurements of the light energy within frequency bands. The particular capture and formation of the spectral representation can vary, and in particular, may be tuned for a particular application. The technologies in Ser. Nos. 13/840,451 and 14/201,852 for capturing spectral information are examples of techniques usable to discern information coding that uses the spectral differences to convey information within images. We describe its application to information coding and decoding in further detail below. We also describe other techniques for information coding and decoding in spectral differences.

One aspect of the invention is a method for encoding an information signal in spectral differences within an image signal, the method comprising:

generating an information signal;

mapping the information signal to locations within a host image signal; and at the locations, inserting the information signal by computing values for color components at the locations so as to form a spectral difference signal that conveys the information signal within the host image, the spectral difference signal representing a distinguishable spectra between two or more colors that appear similar in the human visual system at the insertion locations within the host image signal.

In one embodiment, the distinguishable spectra comprise distinguishable spectra of a first color channel relative to a second color channel, which are metameric pairs. In particular, one example is where the first channel comprises a K channel, and the second channel comprises a combination of C, M and Y channels.

Another aspect of the invention is a method of decoding an information signal comprising:

obtaining spectra of an image signal at locations within the image signal;

discerning a spectral difference signal at the locations, the spectral difference signal representing a distinguishable spectra between two or more colors that appear similar in the human visual system at the locations within the host image signal; and decoding an information signal from the spectral difference signal.

In one embodiment, the method of discerning the spectral differences comprises determining whether a spectra at a location is one of a particular set of distinguishable spectra. The particular set of distinguishable spectra may include a first spectra with a first shape, and a second spectra with a second shape. For example, the first shape is characterized by extent of variations over plural spectral bands (e.g., lumpiness), and wherein the second shape is characterized by absence of variations over plural spectral bands (relative flatness).

The first shape corresponds to a first combination of color channels, and the second shape corresponds to a second combination of color channels. For example, in one embodiment, the first combination comprises a K channel, and the second combination comprises a combination of C, M, and Y channels.

These are but a few inventive aspects disclosed in this document, and are not intended to be limiting to the various inventions described in the following description, which encompasses related work incorporated by reference.

The foregoing and other features and advantages of the present technology will be more readily apparent from the following Detailed Description, which proceeds with reference to the accompanying drawings.

DETAILED DESCRIPTION

Figure 1:
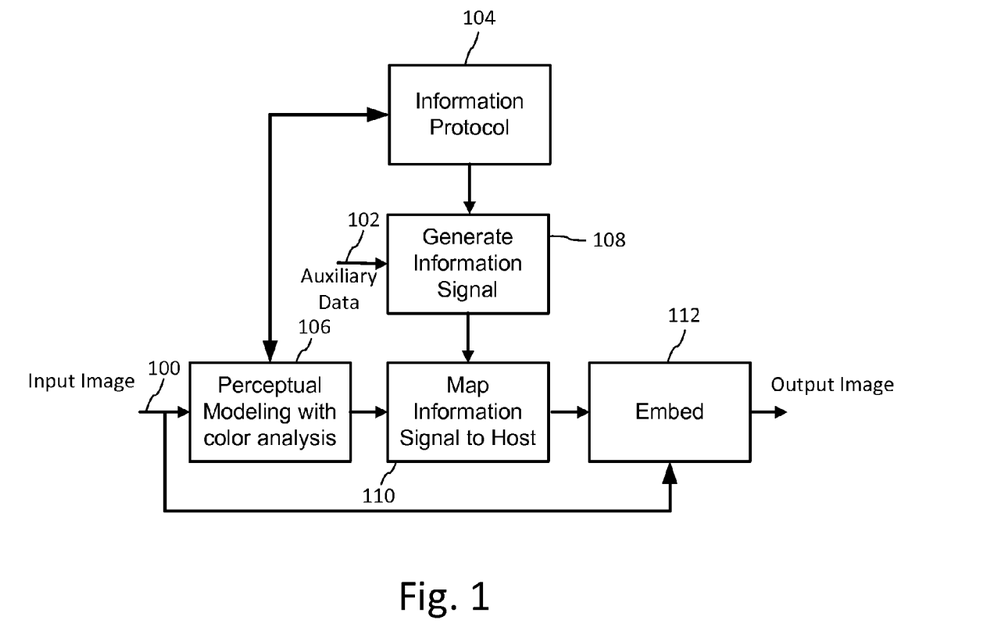
FIG. 1 is a block diagram of a method for coding information into image content.

FIG. 1 is a block diagram of a method for coding information into image content. The input to the method includes an image signal 100, auxiliary data 102 and information protocol 104. The image signal 100, while typically in digital form, may be in various forms and formats. Indeed, the method may also apply to image waveforms in various states, such as signals for applying ink in a printing subsystem, or generating light from a color light source. The input image signal 100 may be a time varying signal, such a sequence of video frames, or a static image. The method applies to image signals with color components, and as noted above, there are a myriad of ways of representing such signals. Generally, such representations comprise color variable values varying over a coordinate space, such as a 2D or 3D image space (spatial coordinate space, spatial frequency space, etc.), possibly including a time varying dimension.

The auxiliary data refers to the information to be encoded in the information channel within the image content. It, too, may be represented in various formats, waveforms, data structures, etc. compatible with the particular information channel and application.

The information protocol 104 specifies the coding format or structure of the auxiliary data. While the data and its protocol are shown as inputs, either of them may be fixed to predetermined data and protocols, which are pre-programmed or set within the circuitry that implements the method. We show the information protocol as an input, in this depiction, to reflect that it may be variable, for a variety of reasons. One example is that an image signal may constitute two or more channels of auxiliary information, each with similar or distinct information. As noted, the color values in a color space and other image variables provide degrees of freedom that may be modulated or otherwise act as data carriers for information channels. Another example is that the information protocol may be designed to adapt to the particular image content, or type of information being conveyed. For instance, the perceptual analyzer 106 may include an image signal classifier that classifies image type and selects an information protocol best suited for the image signal type (e.g., color content, noisy image or high activity measure, smooth image, predominantly text, etc.). Because the information protocol may vary due to image analysis, and/or selectively dictate the type of image analysis that is performed, we have shown a bi-directional flow of data and control between the information protocol block 104 and image analysis block 106.

Another example of a role that the information protocol fulfills is as enabler of security. To this end, the information protocol may support various security protocols, that enable use of the channel for conveying digital signatures, user or device authentication, data integrity checking of the host image, key distribution (e.g., for watermark channels, encryption, digital signatures, secure hashes, etc.), and various forms of encryption, compression, error checking, and error detection used to implement these schemes.

A perceptual analyzer 100 analyzes the input image signal as a pre-processing step to embedding the auxiliary data in that signal according to the information protocol 102. The field of perceptual analysis and modeling has provided extensive teachings for auxiliary data encoding within image signals to achieve desired information coding while adhering to visual quality constraints. Some examples of perceptual modeling are detailed in our prior patents, e.g., U.S. Pat. Nos. 6,590,996, 6,631,198, and 7,352,878, which are hereby incorporated by reference. We anticipate that many such modeling techniques may be applied in conjunction with this method. As several embodiments leverage the fact that humans cannot distinguish certain colors with different spectral distributions, e.g., as a result of metamerism, we anticipate that various forms of information will be embedded in images in an imperceptible way using differences between spectral distributions of such similar looking colors to convey auxiliary data signals. As such, perceptual modeling that is typically now performed in digital watermark applications that do not fully exploit information hiding capacity is not necessarily needed or useful. Indeed, as described below, the resolution of the elements of an encoded data signal may be increased or decreased to suit application constraints without impacting visual quality because the encoded signal remains imperceptible due to metamerism, yet is detectable through various inventive techniques detailed further below, in conjunction with image capture technology in the patent literature that is incorporated by reference.

Since the method relates to encoding information in spectrally different yet visually similar colors, we focus primarily on analysis that relates to this encoding and complementary decoding. As described in U.S. Pat. No. 6,590,996, watermark encoding may be color adaptive, meaning that the data signal may be conveyed in different colors within the image signal depending on the color signals already present. For instance, adjustments of a color component or adjustments along a color direction vector may vary depending on the input color at an embedding location or region. Also, the data signal amplitude and/or shape may also vary based on host signal amplitude or shape such that the net visual impact after data insertion is zero, substantially zero, or within a perceptual threshold metric.

The perceptual analyzer 106 provides an output defining the opportunity for data insertion within a visual impact constraint, whatever that may be for the application. One way of representing this data insertion opportunity metric is as an array of values characterizing the embedding envelope within the image signal in a coordinate space where the data signal is inserted. The array coordinates are specified in relation to embedding regions or locations in the coordinate space of the data channel. Implementations of this opportunity metric are sometimes referred to as perceptual mask. The mask, in this case, defines colors, color directions, and thresholds for these variables that set forth the channel in which changes can be made to insert a data signal while staying within the visual impact constraint. The embedding opportunity metric is designed according to the way in which image parameters are adjusted to insert the data signal. For example, if a ratio between colors at a location or different locations is adjusted, the embedding opportunity specifies a threshold for the amount of the adjustment. If color values are quantized to discrete levels corresponding to the data signal, the embedding opportunity metric sets constraints on the quantization level. Similarly, if relationships among color values or functions of color values for image regions are adjusted to insert data, the embedding opportunity metric sets constraints on the data signal waveform over that region in terms of amplitude, shape, direction in the coordinate space, etc. as the case may be.

If embedding is implemented at a lower level control over rendering of the image signal, the perceptual analyzer can likewise specific commensurate detail over the bounds of the data insertion envelope. For print technologies, this can include halftone conversion parameters like halftone screen selection, line screen angle, halftone dot size, shape, pattern, etc.

Referring again to FIG. 1, the perceptual analyzer 106 represents one functional process flow, while the data signal generation represents a second process flow. In the data signal generation process, the auxiliary data is converted into a data signal for insertion into the image based on the information protocol. These functions may operate relatively independently, at different rates, and in parallel. The perceptual analyzer may be executed more frequently if it depends on the underlying variation in the image signal. If the image signal is constant, with respect to the parameters of the image that define the data channel, then the perceptual analyzer need not be repeatedly executed, and instead, its output may be re-used so long as the parameters of the data channel remain relatively constant.

The data signal generator 108 need only operate at the rate at which the data signal is updated. The data signal may be replicated in spatial and/or temporal blocks (or other data arrangements compatible with the coordinate space of the data signal, information protocol, embedding opportunities, and data insertion technique). The data signal generator takes the input of auxiliary data 102 and converts it into a data signal that adheres to the information protocol 104.

There are a variety of processes that may be used to code the auxiliary data. One aspect of the signal generation process is making the signal more robust to distortion, including robustness to noise, geometric distortion, compression, etc. Techniques for data signal coding include error correction coding, data signal modulation (e.g., spread spectrum, frequency, phase modulation), and various combinations of these methods. Robustness can be enhanced with these data coding techniques as well as with synchronization techniques and combination of the data signal with additional signal to facilitate detection, synchronization and decoding of the auxiliary data. For examples of such techniques, please see U.S. Pat. Nos. 6,590,996, and 6,614,914, which are incorporated by reference.

The output of the perceptual modeling 106 is used to control insertion of the data signal output of the data signal generator 108 in a host image signal. The data signal is mapped to insertion locations via signal mapping function 110. This mapping function may be implicit in the formation of the data signal, as it may be formed as multi-dimensional arrays of values at coordinates that corresponds to insertion locations. Likewise, the embedding opportunity metrics from the perceptual modeling can be structured to provide control parameters (such as embedding thresholds) corresponding to colors at coordinates of the insertion locations. These insertion locations may be regions within a signal, such as contiguous groups of coordinates, interleaved coordinates, or coordinates in some other arrangements, such as random or pseudo random arrangements. These regions may be adapted to the host image, such as by mapping to the shapes and boundaries of objects in an image scene. The regions may also correspond to structures independent of the objects within the image, such as grid like structures, or concentric rings used to encode data, similar to 2D bar codes. The coordinate space may include multiple dimensions of colors (including color vectors within color space corresponding to direction of data modulation), spatial position, transform domain, temporal domain, frequency domain, etc.

The embed function 112 inserts the mapped data signal into corresponding insertion locations within the host signal, while adhering to the constraints, controls and or instructions of the embedding opportunity metrics. This embedding process inserts a data signal in detectable spectral differences. These differences may be relative to a reference that is fixed or variable. For example, colors may be selected or adjusted so as to create a spectral difference between spectral property detected at one embedding location and a fixed reference distribution. Relative differences of spectral distributions may also created at:

1. an insertion location (e.g., differences between spectral distributions of color component selections that may be selectively applied to that location),
2. between insertion locations (e.g., differences between spectral distributions of colors at corresponding pairs or sets of locations),
3. between groups of insertion locations (e.g., differences between spectral distributions of colors at corresponding regions or at recognizable image objects within a scene depicted in the image or video sequence), and/or
4. various combinations of the above.

After the embedding process is applied to the host signal, the embedder outputs the image. As noted, the embedding process may be performed at the point where the image signal is converted into an output form or in its physical formation from different colored materials or light waveforms, such as where it is printed, displayed or otherwise rendered into some physical output signal. It may also be performed earlier, when the host signal is in a higher level digital representation, such as a color digital image signal format. In a hybrid approach, the host image is perceptually analyzed, e.g., while in a higher level color image format, and then the data signal is inserted at or near the point of forming the physical image, to enable greater control over how the spectral differences that carry the data are formed within the analog output form of the image signal.

In the case of objects, these spectral difference properties may be introduced by applying colored materials (e.g., printing inks), assembling the object from colored materials with corresponding spectral distribution properties (e.g., 3D printing, laminating, depositing colored materials, injecting materials into molds, applying coatings or varnishes, with different translucency and surface structure, surface texture formation, etc.), or selectively removing colored materials or varying surface topology (e.g., engraving, etching, laser writing, etc.).

In the case of displayed images, these properties may be introduced by selectively turning on or off illumination from different light sources, combining light sources of different colors, projecting onto different colored materials, passing light emitted from a light source through various color filters, etc.

Figure 2:
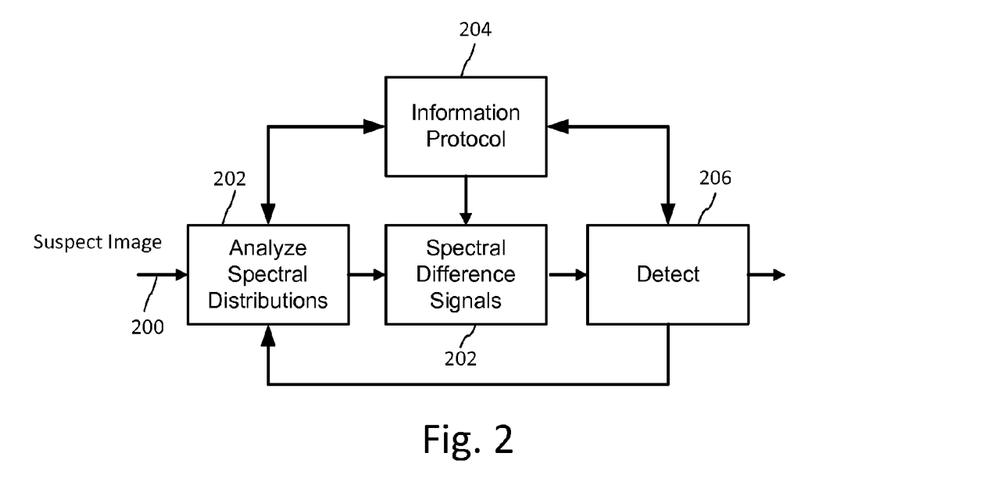
FIG. 2 is a block diagram of a method for decoding information that is embedded in relationships among spectral distributions within image content.

FIG. 2 is a block diagram of a method for decoding information that is embedded in relationships among spectral distributions within image content. First, an image 200 suspected of containing an encoded data signal ("suspect image) is captured. As detailed in further examples below, the capture method and associated signal processing provides spectral distribution data for locations within a captured image signal. The image may be captured from any object or displayed signal that has been formed so as to encode data in the spectral distribution properties of the image.

Next, the spectral distributions for locations within the captured are analyzed (202). This process may include various pre-processing stages, such as filtering and signal transforms. Filtering may be used to remove noise and other un-wanted signal components of a signal representing the spectral data sought. The objective is to yield spectral data from which spectral differences carrying a data signal can be distinguished. Signal transforms may be used to convert the image into a coordinate space and resolution (or variety of resolutions), where signal detection operations are executed.

A spectral distribution for a corresponding location provides a representation of the signal in spectral bands. For this application, the objective is to discern auxiliary signal by differentiating between colors that look the same to humans, yet have different spectral distributions. The spectral distribution data, thus, need only be sufficient to differentiate spectral distributions. As noted, depending on the encoding scheme, this may involve distinguishing from among two or more spectral distributions at an insertion location, or differentiating spectral distributions at different insertion locations (e.g., an image region may appear to be a uniform color, but that color was printed by selectively applying different inks of the same color but different spectral distribution at locations within that region). The number of bands needed per location, therefore, depends on the number of bands needed to distinguish spectral distributions.

Similar to the insertion process, the information protocol 204 may inform how the input data is analyzed to isolate features from which the data signal is extracted, as well as inform selection of the information protocol used to extract the data. In the former case, the information protocol provides guidance to the analysis as to where a data channel resides. There may be an initial data channel with a corresponding protocol, which leads to extraction of one or more additional data channels encoded with different protocols. In the latter case, preliminary analysis of the image content provides a predictor of the information protocol that was applied in the data insertion process. As such, the data and processing control path between image analysis 202 and information protocol 204 blocks are depicted as bi-directional. There may be parallel processing of image analysis, including image analysis that informs protocol selection, and protocol selection that initiates image analysis. Further, when a data signal is detected (e.g., in part of an image or initial frames of video input), and/or at least partially decoded, the results of this detection and decoding may be fed back to the selection of protocol in block 204 as well as the image analysis block 202 to control image analysis.

The information protocol 204 also informs the process of determining spectral differences (206). The information protocol specifies how the data is arranged and encoded in relationships among insertion locations and/or in distinctions between possible distributions detected at insertion locations. The processing in block 202 provides raw estimates of these spectral properties to a detect function 206.

The detect function operates on the raw estimates to detect initial evidence of a data signal. From this initial estimate, it determines its orientation and location, and then proceeds to decode the auxiliary data. This processing may be implemented in a similar fashion as detecting a digital watermark signal, and extracting a coded auxiliary data message from it. Examples of such techniques are detailed in U.S. Pat. Nos. 6,590,996, and 6,614,914, incorporated previously.

The functional blocks shown in FIGS. 1-2 may be implemented as instructions executing on a processor (e.g., CPU, GPU, DSP, etc.), implemented in digital logic circuitry (e.g., as an ASIC), or combinations of both (e.g., an ASIC communicating with processor, and memory for instructions, image data, auxiliary data, and protocols).

U.S. Pat. Nos. 6,721,440 and 6,763,123, which are incorporated by reference, teach a form of encoding and decoding information in image signals that we refer to as "out of phase" watermarks. The concept behind the phrase, "out-of-phase," is that the auxiliary data is encoded in signal components that are out of phase with respect to each other. For example one watermark signal is inverted relative to the other signal, which has the effect of canceling or minimizing the visibility of the watermark in a host image signal. Examples include embedding one component in a combination of CMY color components, and an opposite component in the K-channel, such that the net change in luminance is zero, or nearly zero. While visibility of a luminance change is minimized or eliminated by these offsetting adjustments to different color channels, the data signal can be enhanced by subtracting corresponding components from each channel.

We sometimes refer to "out-of-phase" approaches that use the K channel as 'K-phase Digital Watermarking' or just K-phase. The above cited US patents, namely U.S. Pat. Nos. 6,721,440 and 6,763,123, teach how the use of black ink in classic CMYK printing can be effectively interchanged with a combination of Cyan, Yellow and Magenta, with each being capable of producing an identical visual appearance to an average observer of a print. These patents describe various techniques to extract the information encoded in the out of phase components in an image. One technique uses an infrared camera for capturing the data signal embedded in the K-channel based on the observation that infrared illumination emphasizes the black color plane. See, in particular, U.S. Pat. No. 6,763,123.

Additional work related to out-of-phase signaling within images produced techniques for watermarking in different color channels, and also leveraging out-of-phase signaling in video. See, for example, U.S. Patent Publication 20110216936, which is hereby incorporated by reference. In 20110216936, out of phase watermarks are inserted in different color channels. For example, watermark signal, w, is added in a "a" chroma channel, while w is subtracted from a "b" chroma channel. In this particular approach, no modification is made in a luminance channel, such that the formula for embedding is: (L, a+w, b−w), where the Luminance (L) and chroma channels (a and b) are vectors corresponding to space and/or time coordinates in the image signal.

One approach for encoding information in and decoding information from spectral differences in an image signal leverages the fact that a combination of CMY and K both produce black to humans, yet have spectral differences that are exploited to encode auxiliary data in the host image signal. A K-patch and a CMY-combo-patch can be interchanged in a given print. A 'reading' of the patch differences can be accomplished using only visible light. One of the goals of this approach, among many, is the targeting of garden variety RGB cameras as a reading device.

Figure 3:
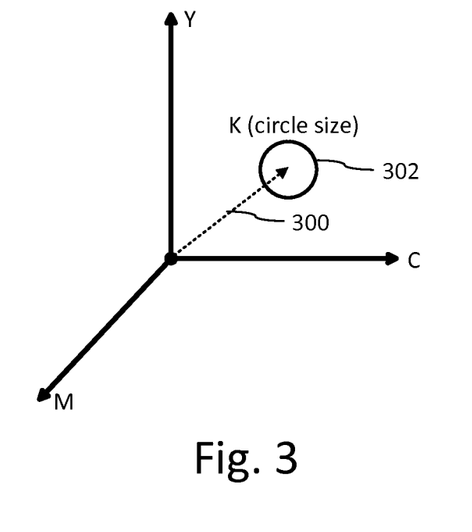
FIG. 3 is a diagram depicting a multi-dimensional color space to illustrate techniques for creating a data channel within a color image signal.

FIG. 3 is a diagram depicting a multi-dimensional color space to illustrate techniques for creating a data channel within a color image signal. Color images are rendered using 4 color channels corresponding to four inks in this case, C, M, Y, and K. C, M, and Y colors are labeled on corresponding axes. A particular color to be printed at a location on an object, for example, is represented digitally by 4 values. Three of the values, C, M, and Y, are depicted by vector 300. The K channel value is depicted as the size of the circle 302. Multiple inputs in this color space (CMYK combinations) map to an equivalent color output in the Human Visual System (HVS) space. This many to one mapping allows our methods to select pairs or sets from the many combinations that represent the same color to encode our information signal without changing the visual appearance of the image when rendered. In particular, in this example, the amount of CMY vs. K is adjusted creating different combinations of CMYK, yet these CMYK combinations look the same when printed. Yet, these different combinations have distinguishable spectra. Using a capture process that distinguishes the spectra, our method is able to analyze spectral differences, detect the information signal encoded in the spectral differences, and then reverse the information coding process to decode a data stream.

We refer to some of our techniques as "Metameric Digital Watermarking," as these techniques enable us to produce prints with effectively completely imperceptible watermark signals to human vision, yet these watermark signals are completely readable by visible light cameras. As noted in the background, metameric is a term used in the color sciences and effectively means 'same color'. It is often used more broadly to mean 'same appearance' though some underlying property, such as ink type or paint formula or plastic additive, is different. It looks the same to the eye, but via some separate analysis, a difference will be found. Metameric failure occurs when a condition, such as the illumination type or application to certain material types, cause colors that otherwise appear to be the same, to appear different.

Illuminant metameric failure can be seen with many different spot color combinations i.e. two colors which appear visually the same under one type of illumination but are different under another type of illumination. Examples of this are color patches which are created to measure the illumination color temperature. For example, the color patches will appear the same under daylight, but different in tungsten or office fluorescent lighting. Illuminant metameric failure can be forced by controlling the illumination in a way that forces color differences to appear to a viewer, a sensor, or both. One technique for forcing a metameric failure is to control the illumination of different color light sources, such as arrays of LEDs.

Switching of combinations of different color light sources may be used to expose spectral differences to a sensor (such as arrays of different color photodetectors synchronized with the switching), while not revealing those differences to a human viewer. Various combinations of switching of the light sources and light detectors may be used to discern spectral differences. Examples include turning on/off combinations of light sources and light detectors at different times and spatial positions (including switching light sources and sensors at different horizontal/vertical positions in a 2D array (X, Y) and at different depths or distances from an object (Z). Below, we provide additional details demonstrating these techniques, e.g., in connection with our SpectraVu, and S-Zed technology. SpectraVu, using synchronized light source and sensor arrangements, may be combined with S-Zed technology, adding a depth dimension.

An example of metameric colors that can be differentiated by forced illuminant metameric failure is with CMY versus K, as this is the common ink set available in most printers. Combinations of CMY and K can be made which appear the same visually but appear very different under appropriately designed narrow band illumination. This is just one example. With additional color inks, as is increasingly more common in color printers, the options increase for creating colors that appear similar, yet have detectable difference in their spectral reflectance properties.

In the field of color science, there are other forms of metameric failure. Another example of metameric failure is geometric metameric failure. With this type of metameric failure, identical colors appear different when viewed at different angles, distances, light positions, etc. This can be caused by material attributes that induce this type of metameric failure, such as translucency, gloss or surface texture. Examples of materials where this failure is observed include metallic inks or paper, and specialty ink coatings or papers. The 3D sensors described and referenced in Ser. No. 13/842,282 (incorporated below) provide a sensor type that can detect color differences due to this type of metameric failure, possibly in combination with illumination control used to induce or amplify the metameric failure effect for capture by the 3D sensor.

Other forms of metameric failure include field size metameric failure. This occurs because the relative proportions of the three light sensitive cone types in the retina of the eye vary from the center of the visual field to the periphery. The result is that colors that match when viewed as very small, centrally fixated areas may appear different when presented as large color areas.

Several purely visible light approaches for distinguishing metameric colors are described below. One goal of these approaches is to use these discernment capabilities as the basis for embedding and reading signals within images. These embedded signals are sometimes referred to as digital watermarks. Through digital signal processing, discrete elements of a digital watermark signal are inserted at corresponding insertion locations within a host image signal. Examples of such techniques are detailed in U.S. Pat. Nos. 6,590,996, and 6,614,914, incorporated previously.

Digital watermark signals may take many forms, as there are various signaling strategies that may be employed. A few examples include Direct Sequence Spread Spectrum, Frequency Hopped Spread Spectrum, Frequency Shift Keying, and Phase Shift Keying. Various forms of carrier signals and carrier signal modulation may be employed, e.g., to modulate a carrier with a data sequence. Examples of signal modulation techniques include amplitude, phase, and frequency modulation. See, U.S. Pat. No. 6,614,914 for some examples of signaling strategies, carrier modulation, and data insertion functions. The possibilities for watermark signal generation are quite broad, and these are but a few examples.

In digital signal processing implementations, the resulting watermark signal is in the form of a discrete, digital signal. Regardless of how the signal is generated or structured, it comprises discrete elements when implemented in digital logic or programmable digital processors. These elements may correspond directly to elements of the message symbol encoding strategy, such as chips of a spread spectrum type signal. The discrete elements may simply be discrete samples of a digital representation of the watermark signal, without such a direct correspondence to message symbol elements.

The insertion function, which is used to insert a discrete element or group of such elements at a corresponding insertion location, may also vary. As describe previously, this function can be an addition of the discrete element to a corresponding color component, substitution, or some other linear or non-linear function, taking into account or not, a masking function. Quantization techniques, for instance, quantize a host signal attribute at an insertion location according to the corresponding watermark signal element.

We sometimes refer to discrete elements of a watermark signal as waxels, and the spatial scale of the elements, relative to a spatial coordinate space of the host image signal, as the waxel size. The mapping function of FIG. 1 may be implemented in an operation in which the discrete elements of the watermark signal are mapped or assigned to spatial locations or regions (e.g., patches) of the host image signal, which we refer to as a waxel. At this waxel, the insertion function selects or modifies the color components to correspond to a particular spectra, which is distinguishable from color components represent the same color in HVS. The net effect of these modifications is to create a spectral difference signal at the waxels. Waxel is a variant of the commonly used term, "pixel," representing a discrete image element. In some of our earlier patents, we refer to elements of the watermark signal as "bumps" and bump sizes. See for example, U.S. Pat. No. 6,122,403, which is hereby incorporated by reference. These "bump" elements may have various shapes and map to corresponding regions of pixels in the host image, as illustrated in U.S. Pat. No. 6,122,403 (see, e.g., FIGS. 21A and 21B). Of course, similar concepts apply when the watermark signal is inserted in domains other than a spatial domain, like frequency domains, and other transform domains. The reader can refer to our US patents (e.g., U.S. Pat. Nos. 6,122,403, 6,590,996, and 6,614,914) and literature on digital watermark (DWM) technology for details on how such signal modulation capabilities can support DWM applications.

Though classic 'CMYK' printing anchors the main explication above and below, those practiced in the arts of printing can appreciate that other combinations of inks can be contemplated and that the number of utilized inks need not be confined to the number four. The metamerism properties, producing like-appearance patches to the human eye yet having some device be able to discern differences, remains an operative goal.

SpectraVu as a Metameric DWM Reader

Our patent application Ser. Nos. 13/840,451 and 14/201,852, entitled Sensor-Synchronized Spectrally-Structured-Light Imaging, provide techniques useful for discerning a pair of metameric colors, such as, a K-patch from a CMY-patch. In lay vernacular, these spectral reader principles will be able to discriminate between the lumpier spectra of a CMY-patch and the smoother spectra of a K-patch.

We now turn to how to use spectral measurements taken from this imaging technology are used to discriminate spectral differences. Generally speaking, as an empirical matter, most black inks have a relatively smooth and largely flat reflectance spectrum. By definition, this is not so with cyan, magenta and yellow inks. When you combine C, M and Y inks, again as an empirical matter, for most commercial and specialty inks one will find some spectral variations relative to the smoother, flatter spectral properties of black ink. In a similar manner, sets of two or more material combinations that produce the same color, yet have different spectral properties, can be used to convey imperceptible information in images by modulating the combination of materials to encode a signal in the spectral differences among the sets. The elementary signaling of the difference signal may be binary (e.g., one combination is detected as dominant over the other) or M-ary (e.g., one combination is detected as dominant over two or more other combinations). This encoding in the difference signal between the two or more sets (e.g., black (B) versus CMY-combo) is precisely the signal that SpectraVu technology can measure.

For example, one may posit a 'B vs. CMY' signal being thus derived from the spectral band measurements of SpectraVu, tuned via correlation operations on the spectral data, producing numerical answers to the question 'what is the black ink to CMY-combo ink ratio?' at each insertion location of a print. The human eye will see the same thing for two opposite regions, yet a SpectraVu enabled camera will discern the lumpy differences in the spectra of K channel ink vs. the combination of CMY ink.

For digital watermark encoding, this concept of different patches of ink is applied at the level of mapping digital watermark elements (e.g., waxels) to host images. The digital watermark encoding process modulates small regions, some tilted toward one color combination (e.g., black ink), some toward another color combination (e.g., the CMY-combo inks), thereby forming the basis of a DWM signal.

The CMY lumpiness signature set against the B smoothness signature is the primary attribute of signal strength and readability of the thus-enabled DWM modulation approach. If the CMY-combo inks get simply too close to the smoothness of the black ink alone, the ability to discriminate goes away, they will look the same to a SpectraVu enabled camera as they already do to the human eye. Thus, the lumpiness in the CMY-combo spectra is desirable, as it enables the information decoding process to detect the auxiliary data signal and extract the encoded data.

S-ZED Sensors and/or Imaging Spectrophotometers as Metameric DWM Readers

Reader is referred to our pending U.S. patent application Ser. No. 13/842,282, entitled NEXT GENERATION IMAGING METHODS AND SYSTEMS, filed Mar. 13, 2013, which is hereby incorporated by reference. In this document, we describe another type of spectrally discriminating sensor. This description is but one example of a class of imaging devices which transcend 'RGB' imaging capabilities and often deal with breaking up visible light into multiple bands of at least 4, and often 10, 20 or even 100 or more. All of these innately spectrally-capable devices can form the basis for spectral difference discrimination, including, but not limited to CMY lumpiness vs. B smoothness.

'Higher Resolution Bayer' Cameras as a Metameric DWM Reader

Yet another way to discriminate spectral differences (e.g., CMY patches from B patches) is to very simply take higher resolution images of patches, usually 2×, 3× or even higher than the innate patches that the human eye will be viewing. A normal Bayer-pattern camera, held close to a print, will do just fine. Again, the ability of the Bayer camera to discriminate CMY from B will be the key driver of signal levels and signal readability.

New Flexibility on Waxel Size and 'Scale' with Metameric DWM

Presuming that metameric pair (e.g., B versus CMY) imperceptibility criteria are superb, i.e., even highly picky printers will be happy with the results, this may open up possibilities to expand the innate scale of waxels from their general 1/100th of an inch square dimension to something higher. This may help in far-camera-distance applications or so-called multi-scale embedding of several signals. In particular, one watermark is embedded at a first resolution for reading from capture devices that are within a nearby range of distances from an image. Examples include a cell phone camera held near a poster, display screen or projection screen of the image containing watermark signals at different resolutions. One or more additional watermarks are embedded at lower resolution (or progressively bigger waxels) for reading at ranges further away (e.g., a cell phone held across the room or at a distance from a billboard or in-store signage).

Testing Procedures for Metameric Patch Discrimination

Metameric pair (e.g., K versus CMY-combo patch) discrimination will be aided by being able to know the precise spectral differences between the two. For readers which are intended to work across a wide range of commercial inks, even here some 'generic average difference' between black inks and CMY-combo inks will be desired. Either way, a spectral difference signal needs to be measured and stored as part of the Metameric DWM reading process. Test prints having very large areas of each type of patch should be printed and their spectral property differences measured. Readers with specific knowledge of specific inks should use empirical data from those known inks. Other broadband WM readers should access commercial-usage averages of these empirical results. Paper type also needs to be considered, i.e. matt versus glossy, as but one additional example.

Unique Identification of Printed Objects

This section appeared in U.S. Provisional Application 61/907,362, filed Nov. 21, 2013, and U.S. application Ser. No. 14/201,852, filed Mar. 8, 2014. It is being included in this document, and related teachings from these prior applications are hereby incorporated by reference.

The identification power of N-D spectral vectors may be leveraged by selecting combinations of inks or ink additives that uniquely identify or discriminate classes of printed objects. Patches of such unique ink formulations may be printed on product packaging for example, to identify it. The use of ink variations, as well as the spatial dimension to vary formulations over different patches, provides additional degrees of freedom to identify a printed item (as a function of spectral composition and location to provide a 2D or higher dimensional spectral code as function of location and N-D spectral vector composition). This application of spectral codes may also be applied in layers applied by 3D printers.

These objects are identified by computing spectral N-D vector images from images captured of the printed object, mapping them to a feature descriptor space, and matching them with reference data in a reference database (using above referenced classification technologies, for example). Alternatively, or in combination, the spectral descriptors may be used to encode data symbols, which are detected using a classifier, then converted to a data symbol and further processed (e.g., using error correction and detection) to provide a robust, variable data signal that can encode an identifier and any other desired metadata.

The standard Pantone spot color set consists of 1114 different spot colors, each mixed from some combination of 13 base inks, plus black. Of these, somewhat over 50% of them can be matched by screening a combination of the standard CMYK process inks. Pantone has a 6 color process, called Hexachrome, which allows screened reproduction of almost 90% of the spot colors. So, one can get around 8 or 9 bits per screened CMYK color "patch", and slightly more for a Hexachrome "patch". The selection of inks may be designed in conjunction with the selection of the LED sensor pairing of a reader device to obtain the desired address space of unique symbols that may be encoded in a particular printed patch.

As another variation, optical nanodot solutions can be added to ink formulations to introduce spectrally distinguishable characteristics. For example, differing ratios of nanodot injected material produces a modulation of the spectral vector of a printed patch, which can be used to encode a data symbol or graphical element of a detectable geometric pattern.

Relatedly, digital watermarks may be encoded in spectral information as disclosed in our related application 61/832,752, which is incorporated by reference. See also teaching of additional signal encoding techniques in Ser. No. 13/964,014 (now published as 2013-0329006), which is also incorporated by reference. The teachings of 61/832,752 and 2013-0329006, can be combined with the technologies in this disclosure to provide a means to identify printed objects using various data encoding techniques, identifying patterns, image recognition in spectral domains, including spectral ratio or spectral differences, as disclosed in these references and this document.

This technology can then be applied in various other industries where such spectral information may be conveyed in colorants, dyes, inks etc., such as food dyes, clothing dyes, colorants for cosmetics, pharmaceuticals, medical diagnostic materials for imaging within the human body, etc.

Regarding medical imaging applications, our techniques of using spectral information, alone or in combination polarimetric information and 2D and 3D spatial, depth (e.g., spectral and polarimetric measurements for pixels at and below skin surface), and can be used to augment approaches such as described in U.S. Pat. Nos. 6,996,549 and 8,543,519, which are hereby incorporated by reference.

Additional Embodiments

The techniques disclosed above, in this section, and in the incorporated documents may be combined in various novel combinations.

Spot colors and their process color or hexachrome equivalents can be thought of as metameric pairs which look similar under daylight but appear very different in narrowband illumination. This can be exploited to encode information into as well as to recognize printed objects of various kinds.

For example, one method spatially varies the combination of spot and process color to create a final color in the image for a printed object. This enables signals of various kinds to be encoded imperceptibly in the imagery and printed on objects, such as product packaging, documents, labels, etc.

Further, encoded signal can be designed to be "fragile" in the sense that it may be detected in some imaging equipment, and not others. For example, such a signal can be designed to not be detected by a broad band RGB sensor, but detectable by narrow band spectra illumination. The spectral curves of the two colors are different since different base dyes have been mixed to create an equivalent color. For example, Pantone 213 on uncoated stock is made of 75% Rhodamine Red and 25% Warm Red, whereas the process color equivalent is 80% magenta and 25% yellow.

Once a palette of possible inks are chosen, the imaging device and associated image process is designed for optimal detection and recognition of the signals encoded in the spectral relationships. In particular, the imaging device is configured with illumination sources (e.g., LEDs) and associated spectral bands to maximally discriminate between chosen ink A and chosen ink B. In case of LED illumination sources in our implementations, the LED bands are very typically 10 nanometer to 20 nanometer band-width, and in general, selecting LED bands at the 'ratio-maxima' of the two ink spectral curves provides effective signal discrimination. For example, in a case where ink A has a reflectance spectrum of 50% at 600 nm, 45% at 620 nm, 40% at 640 nm, 45% at 660 nm, and 55% at 680, etc., then ink B can be selected to have a reflectance spectrum at 50% at 600 nm, 55% at 620 nm, 40% at 640 nm, 35% at 660 nm and then 55% at 680 nm. The imaging device is configured to have LEDs with central wavelengths at 620 nm and at 660 nm, where the ratios (or somewhat equivalently the differences) of the reflectance is maximally discriminating.

The above design of signals using formation of different ink relationships in various spatial arrangements can be used to convey signals that are detectable by machine and or revealed to human viewers under corresponding illumination conditions. In addition to the examples above, yet another example is to use a spectral imager to 'visibly reveal' underlying graphics that are hidden under normal daylight by metamerism. In one embodiment of such a printed object, large inch-scale regions are inked with ink A versus B, driven by some graphics or underlying text. The illumination device (e.g., LED light on a smartphone or mobile device, or illumination within a Point of Sale Imager) illuminates it with the corresponding spectral band or bands, and both visibly as well as on the smartphone screen displaying the captured imagery, overt graphical forms initial hidden by the metamerism become human visible.

The display screen of a display device, such as mobile device screen may be controlled to provide variable spectral illumination for an object, which is then captured in the image sensor of the same or different device. From the captured images illuminated in this fashion, signals conveyed in the spectral differences may then be extracted as detailed in this document, including the material incorporated from other patent documents and publications. For more teaching on use of a display screen as a multi-spectral illumination source, please see our co-pending application Ser. No. 14/276,578, which is hereby incorporated by reference.

These signal encoding techniques may be used to introduce layers of different information for different purposes. A first layer may contain a bar code, another layer a promotional graphic, another layer a counterfeit detection signal, another layer a signal for geometric registration and/or distance sensing. On the latter, for example, larger scale signal encoding can be used to indicate from a distance whether a printed object (e.g., package on a store shelf) is watermarked (or encoded with some other useful signal). Moreover, the spatial configuration of the signal may be used to indicate the correct reading distance for optimum signal detection of watermarks, etc.

CONCLUDING REMARKS

Having described and illustrated the principles of the technology with reference to specific implementations, it will be recognized that the technology can be implemented in many other, different, forms. To provide a comprehensive disclosure without unduly lengthening the specification, applicants incorporate by reference the patents and patent applications referenced above.

The methods, processes, and systems described above may be implemented in hardware, software or a combination of hardware and software. For example, the signal processing operations described above may be implemented as instructions stored in a memory and executed in a programmable computer (including both software and firmware instructions), implemented as digital logic circuitry in a special purpose digital circuit, or combination of instructions executed in one or more processors and digital logic circuit modules. The methods and processes described above may be implemented in programs executed from a system's memory (a computer readable medium, such as an electronic, optical or magnetic storage device). The methods, instructions and circuitry operate on electronic signals, or signals in other electromagnetic forms. These signals further represent physical signals like image signals captured in image sensors. These electromagnetic signal representations are transformed to different states as detailed above to detect signal attributes, perform pattern recognition and matching, encode and decode digital data signals, calculate relative attributes of source signals from different sources, etc.

The above methods, instructions, and hardware operate on reference and suspect signal components. As signals can be represented as a sum of signal components formed by projecting the signal onto basis functions, the above methods generally apply to a variety of signal types.

The particular combinations of elements and features in the above-detailed embodiments are exemplary only; the interchanging and substitution of these teachings with other teachings in this and the incorporated-by-reference patents/applications are also contemplated.

We claim:

1. A method for encoding an information signal in spectral differences within an image signal, the method comprising, with a programmed processor:
generating an information signal comprising message symbols;
mapping the message symbols of the information signal to insertion locations within a host image signal; and
at the insertion locations, inserting the message symbols of the information signal by computing values for color components at the locations so as to form a spectral difference signal between ink applied at a first pixel location and ink applied at a second pixel location to encode a message symbol in relative spectral difference in spectral distribution between the ink at the first and second pixel locations, the computing encoding relative spectral differences at the locations that conveys the message symbols of the information signal within the host image, the spectral difference signal representing a distinguishable spectra between two or more colors that appear similar in the human visual system at the insertion locations within the host image signal.

2. The method of claim 1 wherein the distinguishable spectra comprises distinguishable spectra of a first color channel relative to a second color channel, which are metameric pairs.

3. The method of claim 2 wherein the first channel comprises a K channel, and the second channel comprises a combination of C, M and Y channels.

4. The method of claim 1 the spectral difference corresponds to a pair of inks that appear similar to humans, yet have the spectral difference.

5. The method of claim 4 wherein computing values for color components includes determining the ink and amount of ink in the pair for a location.

6. The method of claim 5 wherein the pair of inks comprise a spot color and process color.

7. The method of claim 6 further including spatially varying a combination of spot and process color in the locations to encode the information signal.

8. A non-transitory computer readable medium, on which is stored instructions, which when executed on one or more processors, perform a method for encoding an information signal in spectral differences within an image signal, the method comprising:
generating an information signal comprising message symbols;
mapping the message symbols of the information signal to insertion locations within a host image signal; and
at the insertion locations, inserting the message symbols of the information signal by computing values for color components at the locations so as to form a spectral difference signal between ink applied at a first pixel location and ink applied at a second pixel location to encode a message symbol in relative spectral difference between the ink at the first and second pixel locations, the computing encoding relative spectral differences at the locations that conveys the message symbols of the information signal within the host image, the spectral difference signal representing a distinguishable spectra between two or more colors that appear similar in the human visual system at the insertion locations within the host image signal.

9. A method of decoding an information signal comprising, with a programmed processor:
obtaining spectra of an image signal at locations within the image signal;
discerning a spectral difference signal at the locations by determining, at the locations, a relative difference between spectral distributions at first and second pixel locations in the image signal, the spectral difference signal representing a distinguishable spectra between two or more colors that appear similar in the human visual system at the locations within the host image signal; and
decoding an information signal from the spectral difference signal by extracting message symbols from relative differences between spectral distributions of different pixel locations and error correction decoding a message from the message symbols.

10. The method of claim 9 wherein the discerning the spectral differences comprises determining whether a spectra at a waxel location is one of a particular set of distinguishable spectra, determining whether a spectra at a different waxel location is one of a particular set of distinguishable spectra, and determining a relationship between the spectra at the first and second waxel locations to extract a message symbol encoded in the relationship.

11. The method of claim 10 wherein the particular set of distinguishable spectra include a first spectra with a first shape, and a second spectra with a second shape.

12. The method of claim 11 wherein the first shape is characterized by extent of variations over plural spectral bands, and wherein the second shape is characterized by absence of variations over plural spectral bands.

13. The method of claim 11 wherein the first shape corresponds to a first combination of color channels, and the second shape corresponds to a second combination of color channels.

14. The method of claim 13 wherein the first combination comprises a K channel, and the second combination comprises a combination of C, M, and Y channels.

15. The method of claim 12 wherein the two or more colors correspond to inks that appear similar to human vision yet have spectral differences, and detecting the information signal includes computing ratio of a measurement of a first and second ink of the inks at a first wavelength and at the locations within the image signal.

16. The method of claim 15 wherein the first and second inks are a metameric pair.

17. The method of claim 15 wherein the first ink comprises a spot color ink and the second ink comprises a process color ink.

18. The method of claim 17 wherein the first ink comprises a mix of spot color components, and the second ink comprise a mix of process color components.

19. The method of claim 12 wherein the two or more colors correspond to a spatial arrangement of first or second visible inks of a metameric pair, which appear to be a similar color under normal lighting, yet have spectral differences that become human visible in response to spectral illumination.

20. The method of claim 18 wherein two or more colors correspond to a spatial arrangement of first or second visible inks of a metameric pair, which appear to be a similar color under normal lighting, yet have spectral differences that are machine detectable in response to controlled narrow-band spectral illumination, and wherein information signal includes a signal from which distance between a camera and object captured by the camera is ascertained, the distance being further used to extract additional information from the image.

21. A non-transitory computer readable medium, on which is stored instructions, which when executed on one or more processors, perform a method of decoding an information signal, the method comprising:
obtaining spectra of an image signal at locations within the image signal;
discerning a spectral difference signal at the locations by determining, at the locations, a relative difference between spectral distributions at first and second pixel locations in the image signal, the spectral difference signal representing a distinguishable spectra between two or more colors that appear similar in the human visual system at the locations within the host image signal; and
decoding an information signal from the spectral difference signal by extracting message symbols from relative differences between spectral distributions of different pixel locations and error correction decoding a message from the message symbols.

22. An image capture device comprising:
an illumination source in communication with a controller for providing controlled spectral illumination;
an image capture sensor for capturing an image signal of an object or scene under the controlled spectral illumination; and
one or more programmed processors configured to:
obtain spectra of an image signal at locations within the image signal;
discern a spectral difference signal at the locations by determining, at the locations, a relative difference between spectral distributions at first and second pixel locations in the image signal, the spectral difference signal representing a distinguishable spectra between two or more colors that appear similar in the human visual system at the locations within the host image signal; and
decode an information signal from the spectral difference signal by extracting message symbols from relative differences between spectral distributions of different pixel locations and error correction decoding a message from the message symbols.

* * * * *